United States Patent
Salamati-Saradh et al.

[11] Patent Number: 5,978,078
[45] Date of Patent: Nov. 2, 1999

[54] SYSTEM AND METHOD FOR DETECTING PARTICLES ON SUBSTRATE-SUPPORTING CHUCKS OF PHOTOLITHOGRAPHY EQUIPMENT

[75] Inventors: Sima Salamati-Saradh, Plano; Douglas E. Paradis, Richardson, both of Tex.

[73] Assignee: Texas Instruments Incorporated, Dallas, Tex.

[21] Appl. No.: 08/992,415

[22] Filed: Dec. 17, 1997

Related U.S. Application Data

[60] Provisional application No. 60/033,110, Dec. 17, 1996.

[51] Int. Cl.$^6$ .................................................. G01N 21/00
[52] U.S. Cl. .......................... 356/237; 356/141; 356/445; 356/337; 356/338
[58] Field of Search .................................. 356/237, 141, 356/445, 337, 338

[56] References Cited

U.S. PATENT DOCUMENTS

| | | | |
|---|---|---|---|
| 4,633,504 | 12/1986 | Wihl | 356/237.5 |
| 4,893,932 | 1/1990 | Knollenberg | 356/338 |
| 5,363,172 | 11/1994 | Tokuda | 355/71 |
| 5,369,272 | 11/1994 | Eguchi | 250/235 |
| 5,515,453 | 5/1996 | Hennessey et al. | 382/141 |
| 5,563,702 | 10/1996 | Emery et al. | 356/73 |

Primary Examiner—Frank G. Font
Assistant Examiner—Reginald A. Ratliff
Attorney, Agent, or Firm—Robert D. Marshall, Jr.; Gerald E. Laws; Richard L. Donaldson

[57] ABSTRACT

A system (10, 110, 210) for detecting particles (144) on a surface of a substrate-supporting chuck (14, 114, 214) including an inspection subsystem (128, 130, 131, 116, 250, 252, 222, 216) for analyzing the surface of the chuck (14, 114, 214) to determine if any particles (144) are thereon, a movable table (16, 116, 216) for holding the chuck (14, 114, 214) to inspect it and for moving the chuck (14, 114, 214) during inspection, and a control unit (22, 122, 222) for moving the movable table (16, 116, 216) relative to the inspection subsystem (128, 130, 131, 116, 250, 252, 222, 216) to inspect the surface of the chuck (14, 114, 214) and to produce an indication signal if a particle (144) is detected on the surface of the chuck (14, 114, 214). A method for detecting a particle (114) on a substrate-supporting chuck (14, 114, 214) of photolithography equipment (18, 118) includes the steps of providing an inspection subsystem (128, 130, 131, 116, 250, 252, 222, 216); using a movable table (16, 116, 216) associated with a stepper (18, 118) to move a substrate-supporting chuck (14, 114, 214) relative the inspection subsystem (128, 130, 116, 250, 252, 222, 216), and using the inspection subsystem (128, 130, 131, 116, 250, 252, 222, 216) and movable table (16, 116, 216) to inspect a surface of the substrate-supporting chuck (14, 114, 214) to locate any particles thereon.

16 Claims, 4 Drawing Sheets

SYSTEM AND METHOD FOR DETECTING PARTICLES ON SUBSTRATE-SUPPORTING CHUCKS OF PHOTOLITHOGRAPHY EQUIPMENT

This application claims priority under 35 USC 119(e) (1) of provisional application number 60/033,110, filed Dec. 17, 1996.

TECHNICAL FIELD OF THE INVENTION

This invention relates generally to the field of semiconductor devices and manufacturing, and more particularly to a system and method for detecting particles on substrate-supporting chucks of photolithography equipment.

BACKGROUND OF THE INVENTION

Many modern electronic systems incorporate various electronic components. For example, personal computers may include electronic components in the form of dynamic random access memory (DRAM) units. Each of the electronic components may include an integrated circuit fabricated on a substrate.

The techniques used in fabricating the integrated circuit on a substrate and packaging it for use with the electronic system are many. As a part of one approach, photolithography may be used to place geometric patterns that define devices onto the substrate surface. The photolithography process may utilize a projection-type aligner.

In a projection type aligner, known as a stepper, an illuminating light is irradiated onto a reticle or the original of a mask on which the patterns have been formed for the formation of a given circuit. The projected image of the pattern is transferred by exposure to a photoresist-coated layer on the substrate. Most of the process may be automated. For example, after a reticle case and a wafer carrier are mounted, the stepper may automatically perform the following functions according to the data and sequence stored in a data file: reticle transport to a reticle stage, wafer transport to the wafer stage, reticle pattern focusing on a wafer surface, reticle and wafer alignment, step and repeat of wafer stage, exposure, wafer transport, and the transport of the next wafer to the wafer stage.

In more recent times, as the pattern dimensions of integrated circuits have increasingly become smaller with higher densities, increased demands have been placed on the optical conditions of the stepper such as the focus for the transfer. A small particle or contaminant on a substrate-supporting chuck for holding the substrate during the photolithography exposure process may cause a number of problems, e.g., inexact focusing that may cause the integrated circuit to fail. Because a particle may cling to the substrate-supporting chucks between the chuck and a substrate being exposed on a stepper, any defect caused by the particle may continue until the next cleaning of the chucks. The delay in cleaning may cause as much as a day's worth of material to be bad. On the other hand, if the routine maintenance of cleaning the chucks is performed unnecessarily, time and resources may be needlessly applied.

Cleaning the chucks frequently involves physically cleaning the chucks with isopropyl alcohol. Even with this cleaning process, it is not guaranteed that all the particles will be removed, and in fact, on occasion, a particle may be added by the operator cleaning the chucks.

One approach to addressing the particle-on-the-substrate problem has been to form pin chucks. Pin chucks have a plurality of pins used to support a substrate. If a particle finds its way to the chucks, it will ideally be located between the pins such that the particle will not cause the substrate to be unlevel with respect to a desired exposure plane. The contamination event is, however, not detected with a pin chuck. Furthermore, as dimensions continue to decrease on integrated circuits while wafer sizes continue to increase, this approach may become more limited.

Another approach in trying to correct for particle contamination of substrate-supporting chucks is to provide for focus compensation. Using this approach, compensation is based on information gathered during the tools processing of the wafer. The approach is limited to the size of the area exposed at a given time and is based on the average value of the focus.

SUMMARY OF THE INVENTION

In accordance with an aspect of the present invention, a system and method for locating particles on substrate-supporting chucks of photolithography equipment are provided that substantially eliminate or reduce disadvantages and problems associated with previously developed systems and techniques. According to an aspect of the present invention, a system for detecting particles on a substrate-supporting chuck includes an inspection subsystem for analyzing a surface of the chuck to determine if any particles are on it, a movable table for holding the chuck to be inspected and for moving the chuck during inspection, and a control unit for moving the movable table to allow the inspection subsystem to inspect the surface of the chuck and to produce an indication if a particle is detected on the surface of the chuck. According to another aspect of the present invention, the inspection subsystem may include a laser-scatter inspection subsystem or a video-based inspection subsystem.

According to another aspect of the present invention, a method for detecting a particle on a substrate-supporting chuck of photolithography equipment includes the steps of providing an inspection subsystem, using a movable table associated with a stepper to move the substrate-supporting chuck relative to the inspection subsystem, and using the inspection subsystem and movable table to inspect the surface of the substrate-supporting chuck to locate any particles thereon. According to an aspect of the present invention, a laser-scatter inspection subsystem may be used that includes reflecting a laser beam off a surface of the chuck with a light detector receiving scattered light when a particle is encountered. According to another aspect of the present invention, a video-based inspection subsystem may be used that includes capturing a visual image, converting it to a digital signal, and comparing the digital signal against a digital template to locate any differences that signify the presence of a particle.

A technical advantage of the present invention is that a particle on a substrate-supporting chuck may be automatically detected and the contamination reported. According to another aspect of the present invention, immediate identification of contamination may stop wafer processing and thereby minimize yield loss. According to another aspect of the present invention, the immediate identification and location of particle on a substrate-supporting chuck allows for its recovery and possible identification of the source of the particle.

BRIEF DESCRIPTION OF THE DRAWINGS

For a more complete understanding of the present invention, the objects and advantages thereof, reference is now made to the following descriptions taken in connection with the acconpanying drawings in which.

DETAILED DESCRIPTION OF THE INVENTION

The preferred embodiment of the present invention and its advantages are best understood by referring to FIGS. 1 through 7 of the drawings, like numerals being used for like and corresponding parts of the various drawings.

Figure 1:
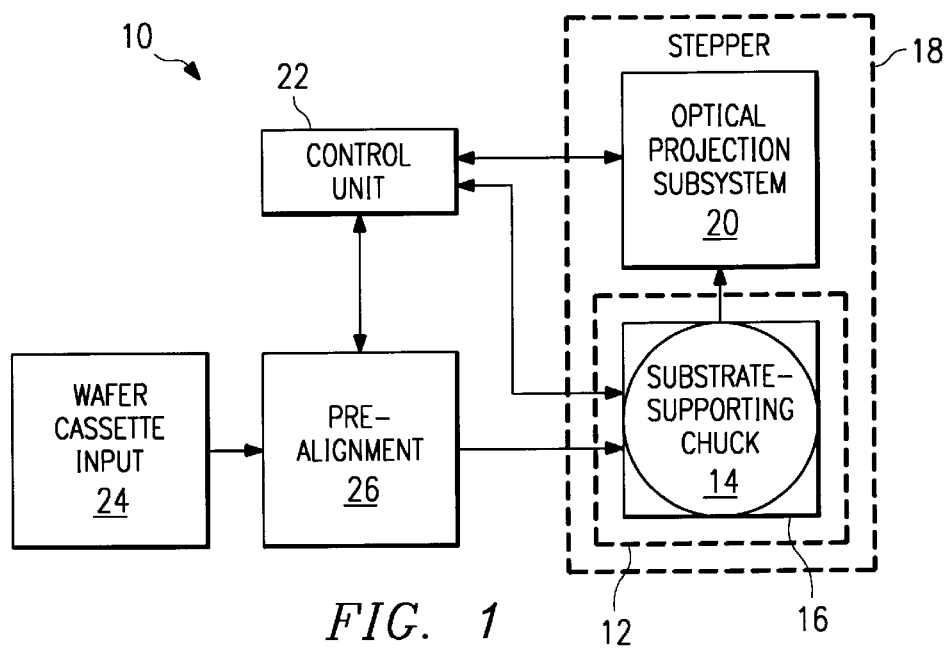
FIG. 1 is a schematic of a system according to an aspect of the present invention.

Referring to FIG. 1, a system 10 for detecting particles on substrate-supporting chucks of photolithography equipment is shown. System 10 includes an inspection subsystem 12 for analyzing a surface of a substrate-supporting chuck 14, which is coupled to a moveable table or stage 16. The inspection subsystem 12 may be formed as an integral part of a projection stepper 18 having an optical projection subsystem 20. Inspection subsystem 12 may be located such that moveable table 16 may be used for both the inspection subsystem 12 and with optical projection subsystem 20 of stepper 18. In system 10, wafer cassette input station 24 may be used to accept incoming wafers or substrates. The substrate may be transferred to a prealignment tower or station 26 and then onto substrate-supporting chuck 14. A control unit 22 having a microprocessor is coupled to inspection subsystem 12, moveable table 16, and optical projection subsystem 20 to coordinate movement and to monitor parameters of system 10. Control unit 22 may also control and monitor prealignment station 26 and wafer cassette input 24 station.

Figure 2:
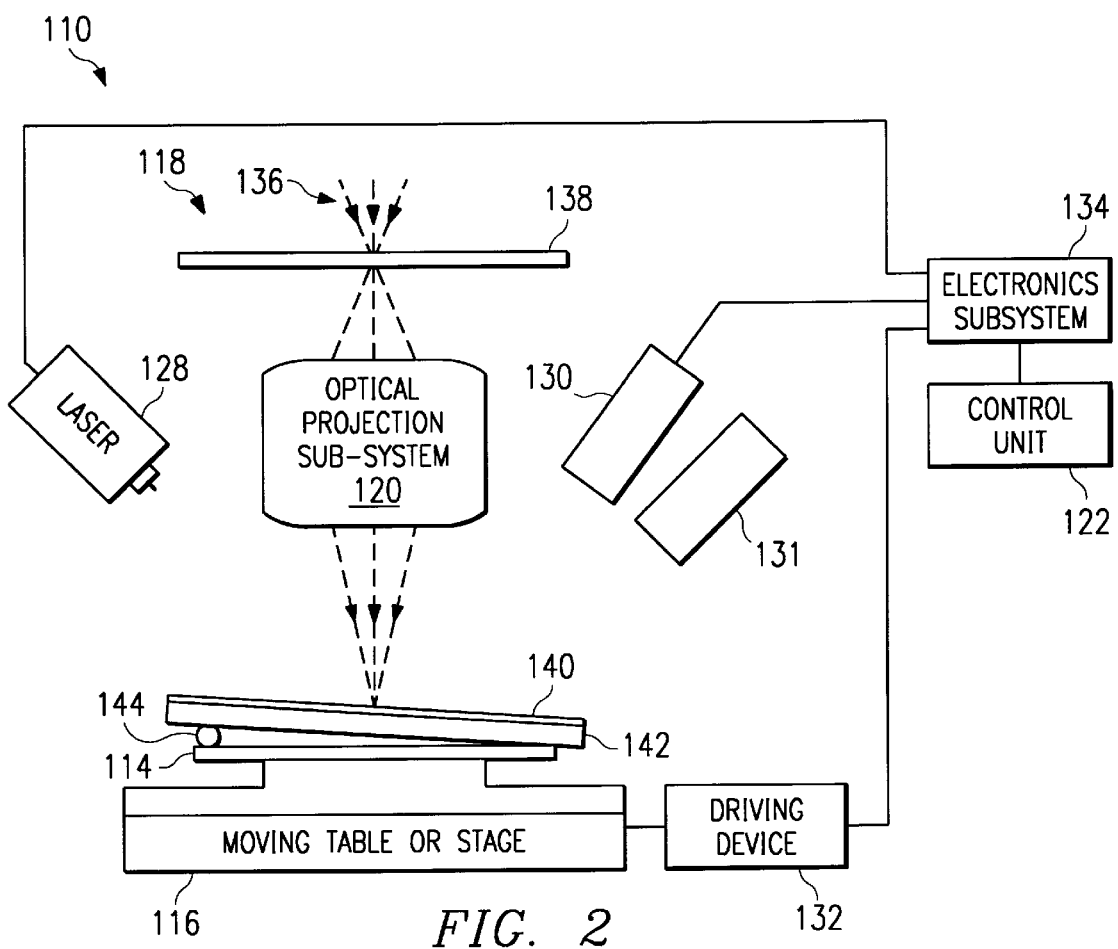
FIG. 2 is a schematic in elevation of a system according to an aspect of the present invention.

Referring to FIG. 2, a system 110 for detecting particles on substrate-supporting chucks 114 of photolithography equipment is shown. System 110 includes an inspection subsystem, which for this embodiment may include a laser 128, a scattered light detector or collector 130 and a beam stop 131. The specific location where laser 128, light detector 130 and beam stop 131 are mounted with respect to components of the stepper 118 (18 of FIG. 1) will vary according to the different types of steppers to which the described system 110 is added or included. In this regard, it is desirable for the stage or table 116 of the stepper to be utilized for inspection as well as for use by the stepper 118 itself. While only one light detector 130 is shown, it is to be understood that a plurality of light detectors 130 may be positioned to detect scattered light reflected off of any particles on substrate-supporting chuck 114. Beam stop 131 is positioned to receive the laser beam from laser 128 after it reflects off substrate-supporting chuck 114. System 110 also includes a control unit 122 and electronics subsystem 134.

Chuck 114 is coupled to a moveable table or stage 116. The substrate 142 is releasably secured on moveable table or stage 116, which can be moved within the XY plane, moved vertically along the axis Z perpendicular to the XY plane, and minutely rotated around the axis Z. The moveable table 116 may be connected to a driving device 132 comprising an X and Y direction driving motors, a Z axis vertical direction driving motor, a Z axis rotation driving motor, and others to perform the exposure position adjustments and to position chuck 114 for inspection. The position of table 116 along each axis may be monitored by interferometers.

The table 116 with precision device driver 132 is under control of an electronic subsystem 134 and is capable of moving chuck 114 under test in a serpentine fashion within a single plane relative to the optical axes of the optical subsystem so that all or any selected part of a surface of chuck 114 may be inspected. Driving device 132 may be coupled to an electronics subsystem 134, which is described below.

System 110 may be incorporated into a stepper 118. Stepper 118 includes a light generating source (not explicitly shown) that develops light 136 used to illuminate a reticle or photomask 138. The desired image of an integrated circuit or device is then projected from reticle 138 to an optical projection subsystem 120 and then onto a photoresist or other photo-sensitizing coating 140 on substrate or wafer 142, which may be, for example, a silicon wafer or gallium arsenide wafer. An autofocus function may be included in stepper 118.

The control unit 122, which includes a microprocessor and memory, performs the sequential controls of the reception, transportation, and positioning of the reticle and substrate 142, and setting and exposure operations of optical systems 120 in response to the various exposure conditions among other tasks. The control unit 122 acts as the operator console and master controller of the system 110. All system interfaces with an operator and facilities are made through the control unit 122. Control unit may include a display and keypad for interfacing with an operator.

Laser 128 and light detectors 130 may be coupled to the electronics subsystem 134 and to control unit 122. The inspection subsystem may be a laser-scatter system and may include software for using laser scattering techniques in conjunction with control unit 122 to locate or detect particles or contaminants on chuck 114.

The electronics subsystem 134 may function to interpret and execute the commands issued by control unit 122. These functions may include: digitize the input from detectors (see FIG. 6), compensate these readings for variations in the incident light intensity, detect defects in the image and transfer the defect data to the control unit 122, accumulate the output of the interferometers used to track the table, provide the drive for driving device 132, and monitor sensors which indicate status.

The exaggerated effect of a particle or contaminant 144 on chuck 114 is shown in FIG. 2. The particle 144 may cause substrate 142 to not be level with respect to a desired projection plane for optical projections subsystem 120. As discussed in the background, this may cause severe defects as the desired integrated circuit pattern is projected onto substrate 142. If after wafer 142 is removed, particle 144 remains on a surface of chuck 114, a defect may be continued until the next cleaning of chuck 114 —and perhaps even after that.

Figure 3:
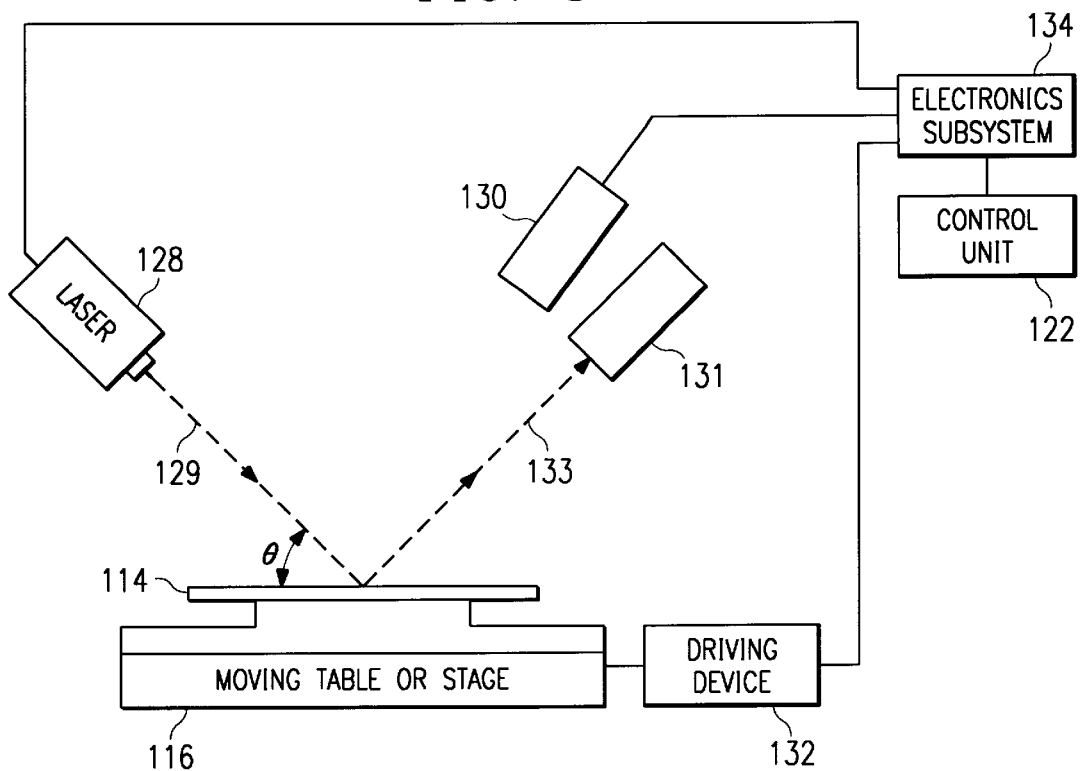
FIG. 3 is a schematic in elevation showing an aspect of the system of FIG. 2.
Figure 4:
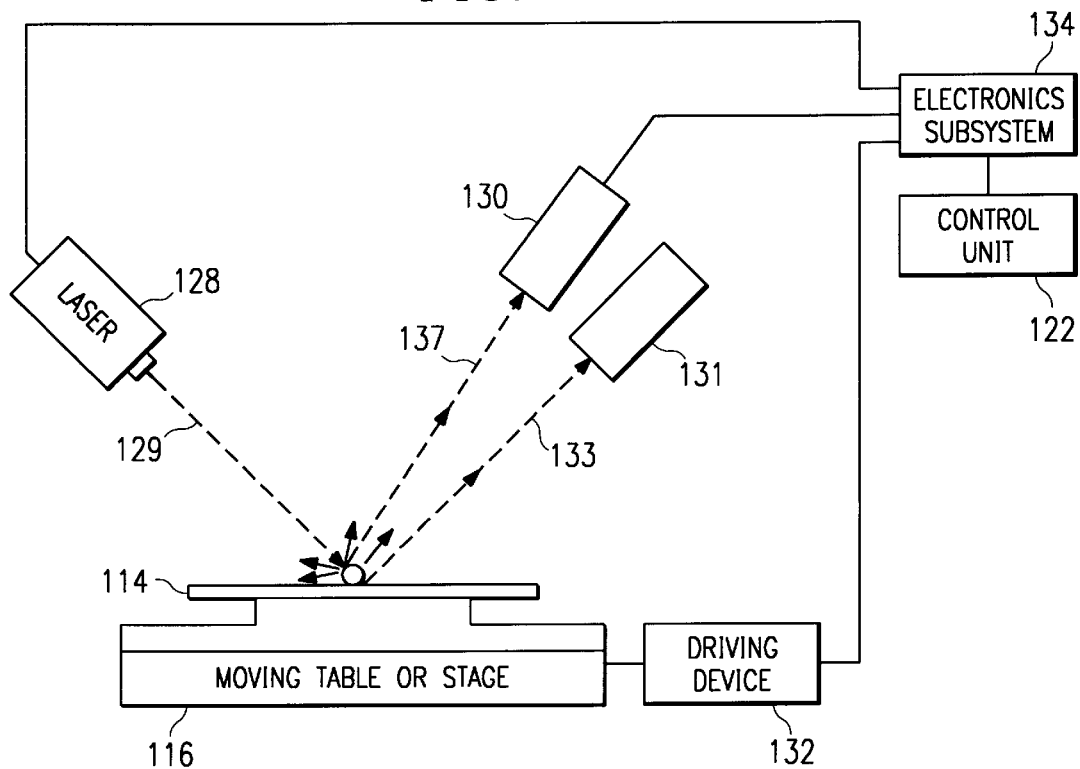
FIG. 4 is a schematic in elevation showing an aspect of the present invention of FIG. 2.

Referring to FIGS. 3 and 4, the inspection subsystem of FIG. 2 will be explained in more detail. In FIG. 3, no particles are observed on chuck 114. The inspection subsystem may determine this by having control unit 122 in conjunction with electronic subsystem 134 cause driving device 132 to systematically drive the chuck 114 in an inspection pattern such that a laser beam 129 emitted by laser 128 is reflected off chuck 114 and into beam stop 131 for all points on the chuck 114. The absence of particles is indicated because no scattered light (above a predetermined threshold) is received by detector 130. Geometries formed on the chuck 114 surface will cause light to be directed towards the detector 130. These geometries are of known size and location and the signal can be predicted and removed by processing the signal in control unit 122 by comparing to a template of the surface of chuck 114. The inspection subsystem is located such that table 116 may be utilized for both the stepper 118 (FIG. 2) and the inspection subsystem thus eliminating the need for a separate moveable table or stage. With the absence of any particles at a given point, such as that shown in FIG. 3, the angle of incidence, theta ($\Theta$), of laser beam 129 provides a predictable location for its reception by beam stop 131, i.e., the beam stop 131 may be positioned at a predetermined location to receive the laser beam 129.

If a particle were to be found on a surface of chuck 114, the fill intensity of the reflected portion 133 of beam 129 would not reach beam stop 131, but would scatter in part such that a portion of the scattered light, e.g., light beam 137, would be received by light detector 130. This is demonstrated in FIG. 4 where beam 129 is shown impacting particle 144 and scattering beam 137 into light detector 130. Because the precise movement of stage 116 is monitored by control unit 122, it allows the exact location of particle 144 to be determined and recorded. The particle 144 may then be recovered by a technician. The recovered particle 144 may then be assayed to determine its likely origination point. This may allow for the source of the contamination to be addressed and perhaps removed so that the particular source of contamination will not be an issue for future processing.

Figure 5:
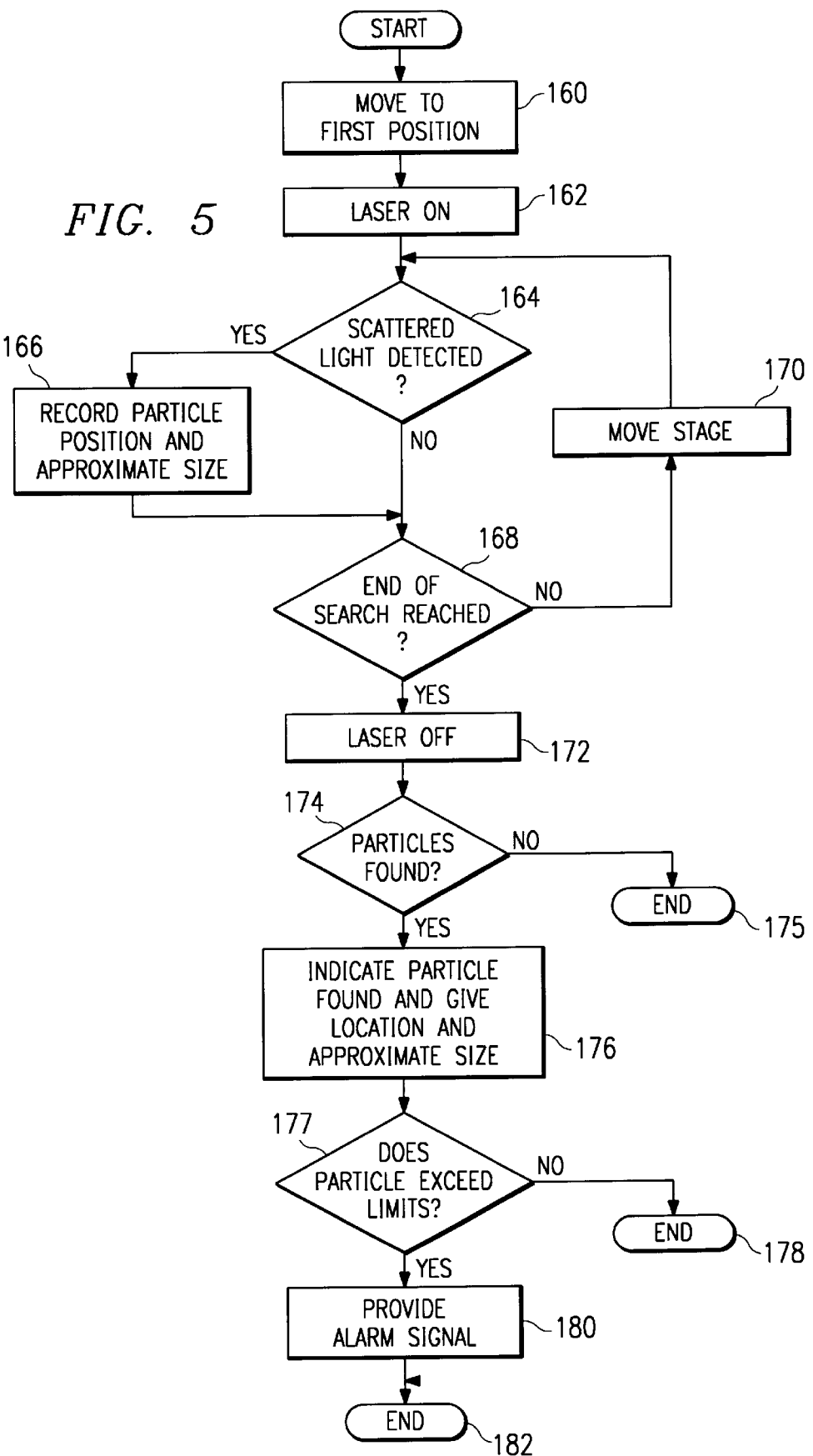
FIG. 5 is a flow chart of one approach for the inspection subsystem.

Referring to FIG. 5, a flow chart is presented for one approach for the inspection subsystem that is shown in FIGS. 2–4 to analyze the surface of chuck 114. The moving table or stage 116 may be brought to a first position to begin a search as indicated at block 160. Laser 128 may then be activated as reflected at box 162. Consideration of whether scattered light detector 130 is receiving scattered light is made at interrogatory box 164. If scattered light above a predetermined threshold is being received, the affirmative response leads to box 166 and the existence of the particle, its position, and its approximate size are recorded and the process flow continues to interrogatory box 168. If the answered interrogatory box 164 is in the negative, i.e., no scattered light has been detected, interrogatory box 168 will also be reached. Interrogatory box 168 addresses whether the end of the search has been reached; that is, has a final position for table 116 been reached or an end of a predetermined search pattern. If the answer to interrogatory box 168 is in the negative, the table 116 may be incremented to the next position in a search pattern as reflected at box 170. If the end of the search has been reached, the answer to interrogatory box 168 will be in the affirmative and the laser 128 will be turned off as reflected at box 172. Thereafter, consideration of whether any particles were found is made at interrogatory box 174. If the answer is in the negative, the search process ends as shown at 175. If particles were found, an indications signal is made that particles were found and the location and proximate size may be given as well as reflected at box 176. Consideration is then given at interrogatory box 177 to whether the particles exceed predetermined limits, i.e., are such a size that they may cause defects.

If the answer to interrogatory box 177 is in the negative, the process ends as reflected at 178. If, however, the answer to interrogatory box 177 is in the affirmative, an alarm signal may be provided as reflected at box 180. Thereafter, the process ends as shown at box 182.

Figure 6:
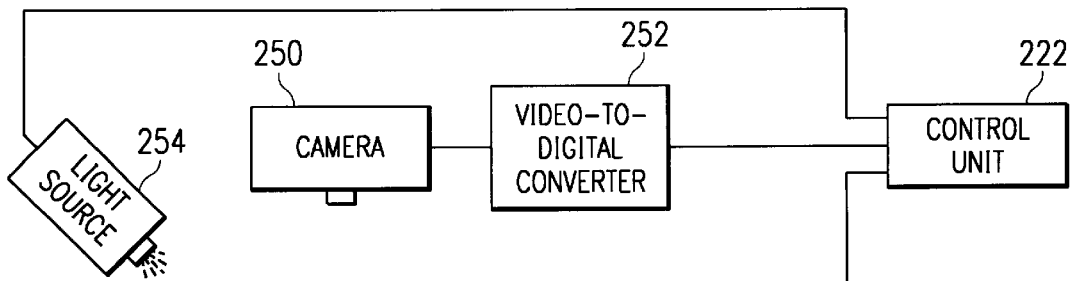
FIG. 6 is a schematic in elevation of another embodiment of the present invention.

Referring to FIG. 6, a system 210 for detecting particles on substrate-supporting chucks of photolithography equipment is shown. Similar to the previous embodiment, a substrate-supporting chuck 214 is coupled to a moveable table or stage 216. Moveable table 216 may be coupled to a driving device 232, which in turn, may be coupled to an electronic subsystem, or, as shown, directly to a control unit 222. System 210 may be formed integral with a stepper, but for simplification, is shown in FIG. 5 without the stepper components such as an optical projection subsystem (e.g., 120 of FIG. 2).

In this embodiment, the inspection subsystem may be a video-based inspection subsystem that may include a camera 250 coupled to a video-to-digital converter 252 for providing a digitized image of all or a portion of a surface of chuck 214 to control unit 222. In capturing the video image with camera 250 and video-to-digital converter 252, a light source, such as light source 254 may be used. Once the digitized video image is delivered to control unit 222, it may be compared with a previously captured video image of a clean chuck 214. The digitized clean chuck image, or template digital signal, may be captured immediately after chuck 214 has been cleaned or is otherwise known to be clean. A bit by bit comparison may be made between the actually captured video image made during the inspection and the template digital signal. Other image comparison techniques may also be used such as a comparison in symbolic space. General reference is made to U.S. Pat. No. 5,515,453 to Hennessey et al., entitled "Apparatus and Method for Image Processing in Symbolic Space," which is incorporated herein for all purposes.

Figure 7:
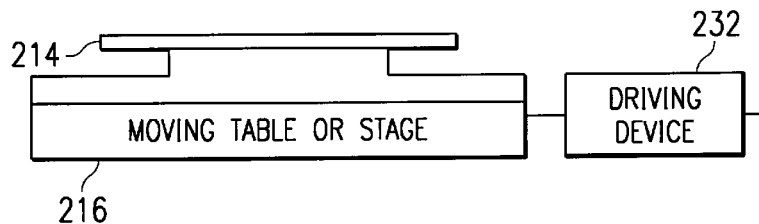
FIG. 7 is a flow chart of another approach for the inspection subsystem.
Figure 7:
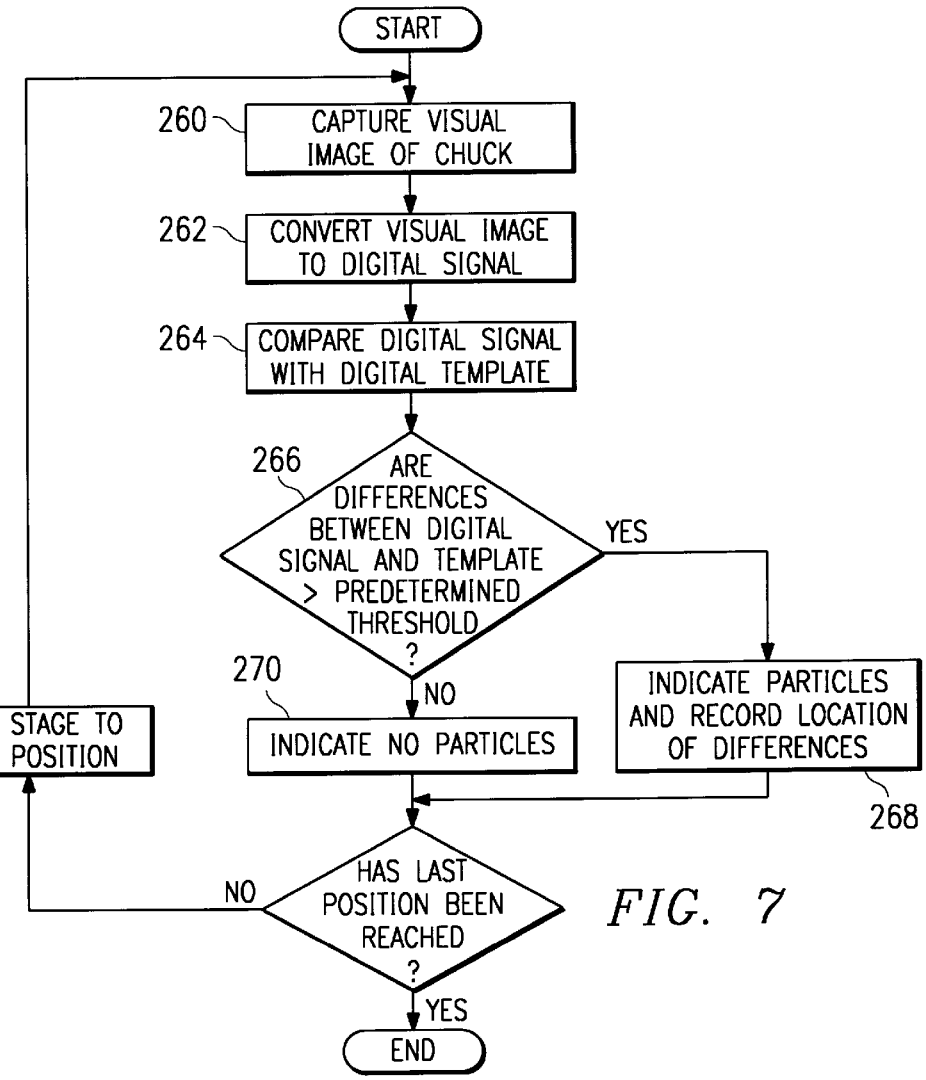

Referring now to FIG. 7, a flow chart of one approach for using the video-based inspection subsystem shown in FIG. 6 is presented. With this approach, a visual image of at least a portion of chuck 214 is first captured by camera 250 as reflected at box 260. The captured visual image is then converted to a digital signal by video-to-digital converter 252 as reflected at box 262. Using the microprocessor and memory of control unit 222, the digital signal may then be compared with a digital template signal, which may be a portion of a previously-recorded digital image of a chuck known to be clean or it may be a CAD-based digital template of what a clean chuck should look like. This latter step is reflected at box 264.

If the differences between the digital signal and the digital template signal are greater than a predetermined threshold, the answer to interrogatory box 266 will be in the affirmative, and a particle is indicated and the location of the particle or the differences is recorded and presented as reflected by box 268 for the captured image. If the differences between the digital signal and the digital template signal are not greater than the predetermined threshold, an indication that no particles exist on the surface of chuck 214 is made at block 270 for the captured image. If camera 250 is able to capture a complete image of chuck 214, they may be accurately compared to the digital template, additional steps may not be necessary. If, however, only a portion of chuck 214 may be captured by camera 250 for processing and comparison with a digital template of a portion of chuck 214, additional steps are necessary so that a search pattern or serpentine pattern of captured images of chuck 214 may be analyzed. In this regard, after boxes 270 and 268, the process flow may continue to interrogatory box 261 where consideration is given as to whether the last search position has been reached for recording a visual image. If the answer to interrogatory box 268 is in the affirmative, the process may end as reflected at box 263. If the answer to interrogatory box 261 is in the negative, the stage may be moved to the next position as reflected at box 265 and the process flow may continue back to box 260 where another visual image is captured at the next location. The loop will continue until interrogatory box 261 is answered in the affirmative. FIG. 7 shows that when a particle is found an indication is provided and its location is provided at block 268, but it is to be understood that if desired, an alarm may be sounded if the differences are greater than a predetermined threshold or limit.

The inspection subsystem using the laser-scatter technique or the video-based technique may be used to locate particles on a chuck 14, 114, 214 as described above. This inspection may be performed after every lot of wafers or after every wafer depending on the frequency of contamination problems. The inspection may occur right after a wafer is unloaded from the chuck or right before the wafer is loaded.

Although the invention has been particularly shown and described by the foregoing detailed description, it will be understood by those skilled in the art that various other changes in form and detail may be made without departing from the spirit and scope of the invention, which is defined by the appended claims.

What is claimed is:

1. A system for detecting particles on a substrate-supporting chuck comprising:
    an inspection subsystem for analyzing a surface of a chuck to determine if any particles are thereon, said inspection subsystem including
        a laser for projecting a laser beam on the surface of the chuck, and
        a light detector for receiving and detecting scattered light from the laser beam after reflecting off a particle on the surface of the chuck;
    a moveable table for holding the chuck to be inspected and for moving the chuck during inspection; and
    a control unit coupled to the inspection subsystem and moveable table, the control unit for moving the moveable table to allow the inspection subsystem to inspect the surface of the chuck and to produce an indication signal if a particle is detected on the surface of the chuck.

2. A system for detecting particles on a substrate-supporting chuck comprising:
    an inspection subsystem for analyzing a surface of a chuck to determine if any particles are thereon, said inspection subsystem including
        a camera;
        a video-to-digital converter coupled to the camera for digitizing a first captured image to produce a first digital signal of the first captured image;
    a moveable table for holding the chuck to be inspected and for moving the chuck during inspection, and
    a control unit coupled to the inspection subsystem and moveable table, the control unit for moving the moveable table to allow the inspection subsystem to inspect the surface of the chuck and to produce an indication signal if a particle is detected on the surface of the chuck.

3. The system of claim 2, wherein the control unit comprises a microprocessor operable to perform the following steps:
    comparing the first digital signal of the first captured image to a second digital signal of a second captured image to identify differences; and
    sounding an alarm if differences between the first digital signal and the second digital signal are greater than a predetermined threshold.

4. The system of claim 2, wherein the control unit comprises:
    (1) a display, and
    (2) a microprocessor operable to perform the following steps:
        (i) compare the first digital signal of the first captured image to a second digital signal of a clean chuck to identify differences; and
        (ii) provide an indication if differences between the first digital signal and the second digital signal are greater than a predetermined threshold.

5. The system of claim 1 further comprising:
    a precision driving device coupled to the moveable table for precisely moving the moveable table; and
    an electronics subsystem coupled to the control unit for executing commands from the control unit.

6. A method for detecting a particle on a substrate-supporting chuck of photolithography equipment, the method comprising the steps of:
    providing an inspection subsystem;
    using a moveable table associated with a stepper to move a substrate-supporting chuck, relative to the inspection subsystem; and
    using the inspection subsystem and moveable table to inspect a surface of the substrate-supporting chuck to locate any particles thereon including the steps of:
        projecting a laser beam onto a surface of a substrate-supporting chuck;
        locating a light detector at a predetermined location to capture and detect scattered light from the laser beam after it reflects off a particle on the surface of the chucks;
        moving the moveable table to cause the laser beam to pass over substantially all of the surface of the chuck; and
        indicating the presence of a particle if any instances are observed where the light detector receives the scattered light.

7. The method of claim 6, wherein the step of using the inspection subsystem and moveable table to inspect a surface of the substrate-support chuck for particles comprises the step of:
    recording the location of any particles indicated in said step of indicating the presence of a particle.

8. A method for detecting a particle on a substrate-supporting chuck of photolithography equipment, the method comprising the steps of:
    providing an inspection subsystem; and
    using a moveable table associated with a stepper to move a substrate-supporting chuck, relative to the inspection subsystem; and
    using the inspection subsystem and moveable table to inspect a surface of the substrate-supporting chuck to locate any particles thereon, wherein said step of using the inspection subsystem and moveable table to inspect a surface of the substrate-support chuck for particles comprises the steps of:
        capturing a video image of the surface of the chuck;
        converting the video image to a first digital signal;

comparing the first digital signal with a template digital signal of a clean chuck; and indicating any differences between the first digital signal and the template digital signal.

9. The method of claim 8, wherein the step of using the inspection subsystem and moveable table to inspect a surface of the substrate-support chuck for particles further comprises the step of:

recording the location of any differences indicated in said step of indicating any differences greater than a predetermined threshold between the first digital signal and the template digital signal.

10. A method of manufacturing a system for detecting particles on a substrate-supporting chuck of photolithography equipment comprising the steps of:

forming an inspection subsystem for analyzing a surface of a chuck to determine if any particles are thereon, said step including forming a laser-scatter subsystem having a laser for projecting a laser beam on the surface of the chuck, and forming a light detector for receiving and detecting scattered light if a particle is encountered by the laser beam;

forming a moveable table for holding the chuck to be inspected and for moving the chuck; and coupling a control unit to the inspection subsystem and moveable table for moving the moveable table to allow the inspection subsystem to inspect the surface of the chuck and to produce a warning signal if a particle is detected on the surface of the chuck.

11. A method of manufacturing a system for detecting particles on a substrate-supporting chuck of photolithography equipment comprising the steps of:

forming an inspection subsystem for analyzing a surface of a chuck to determine if any particles are thereon, wherein the step of forming the inspection subsystem comprises the step of forming a video-based inspection subsystem having a camera and a video-to-digital converter coupled to the camera for digitizing a first captured image to produce a first digital signal of the first captured image;

forming a moveable table for holding the chuck to be inspected and for moving the chuck; and coupling a control unit to the inspection subsystem and moveable table for moving the moveable table to allow the inspection subsystem to inspect the surface of the chuck and to produce a warning signal if a particle is detected on the surface of the chuck.

12. The method of claim 11, wherein the step of forming the inspection subsystem further comprises the step of:

programming the control unit to perform the following steps:

comparing the first digital signal of the first captured image to a second digital signal to identify differences, and providing an indication signal if differences between the first digital signal and the second digital signal are greater than a predetermined threshold.

13. The method of claim 10 further comprising the steps of:

coupling a precision driving device to the moveable table for precisely moving the moveable table; and forming an electronics subsystem coupled to the control unit for executing commands from the control unit.

14. The system of claim 1, wherein:

said laser is disposed to project said laser beam to the surface of said chuck at a predetermined angle;

wherein said system further comprises a beam stop disposed relative to said predetermined angle in the path of said laser beam as directly reflected off the surface of said chuck; and said light detector is disposed relative to said predetermined angle off the path of said laser beam as directly reflected off the surface of said chuck.

15. The method of claim 6, wherein:

said step of projecting the laser beam onto the surface of the substrate-supporting chuck projects the laser beam at a predetermined angle;

said method further comprises the step of disposing a beam stop relative to said predetermined angle in the path of said laser beam as directly reflected off the surface of the substrate-supporting chuck; and said step of locating the light detector to capture and detect scattered light from the laser beam after it reflects off a particle on the surface of the chucks disposes said light detector relative to said predetermined angle off the path of said laser beam as directly reflected off the surface of the substrate-supporting chuck.

16. The method of claim 10, wherein:

said step of forming a laser-scattering subsystem projecting the laser beam onto the surface of the chuck projects the laser beam at a predetermined angle;

said method further comprises the step of disposing a beam stop relative to said predetermined angle in the path of said laser beam as directly reflected off the surface of the chuck; and disposing said light detector relative to said predetermined angle off the path of said laser beam as directly reflected off the surface of the chuck.

* * * * *